(12) United States Patent
Bethke et al.

(10) Patent No.: US 8,371,292 B2
(45) Date of Patent: Feb. 12, 2013

(54) USE OF CICLESONIDE FOR THE TREATMENT OF RESPIRATORY DISEASES

(75) Inventors: Thomas Bethke, Constance (DE); Renate Engelstaetter, Allensbach (DE); Wilhelm Wurst, Constance (DE)

(73) Assignee: Nycomed GmbH, Constance (DE)

( * ) Notice: Subject to any disclaimer, the term of this patent is extended or adjusted under 35 U.S.C. 154(b) by 1074 days.

(21) Appl. No.: 10/571,311

(22) PCT Filed: Sep. 15, 2004

(86) PCT No.: PCT/EP2004/052172
§ 371 (c)(1),
(2), (4) Date: Mar. 9, 2006

(87) PCT Pub. No.: WO2005/025578
PCT Pub. Date: Mar. 24, 2005

(65) Prior Publication Data
US 2007/0025923 A1   Feb. 1, 2007

Related U.S. Application Data

(60) Provisional application No. 60/502,984, filed on Sep. 16, 2003.

(51) Int. Cl.
*A61M 15/00* (2006.01)
(52) U.S. Cl. .................. 128/200.24; 514/1.7; 540/63
(58) Field of Classification Search ............ 128/200.24; 514/1.7; 540/63
See application file for complete search history.

(56) References Cited

U.S. PATENT DOCUMENTS

| | | | |
|---|---|---|---|
| 4,342,603 A | 8/1982 | Daniels | |
| 4,816,445 A | 3/1989 | Mitsuhashi et al. | |
| 5,112,407 A | 5/1992 | Sakai et al. | |
| 5,133,974 A | 7/1992 | Paradissis et al. | |
| 5,178,866 A | 1/1993 | Wright et al. | |
| 5,263,475 A | 11/1993 | Altermatt et al. | |
| 5,434,304 A | 7/1995 | Trofast et al. | |
| 5,474,759 A | 12/1995 | Fassberg et al. | |
| 5,482,934 A | 1/1996 | Calatayud et al. | |
| 5,733,901 A | 3/1998 | Gutterer | |
| 5,795,564 A | 8/1998 | Aberg et al. | |
| 5,811,388 A | 9/1998 | Friend et al. | |
| 5,840,917 A | 11/1998 | Ol et al. | |
| 5,891,844 A | 4/1999 | Häfner | |
| 6,030,604 A | 2/2000 | Trofast | |
| 6,120,752 A * | 9/2000 | Oliver et al. | ............ 424/45 |
| 6,124,268 A | 9/2000 | Ghosal | |
| 6,136,839 A | 10/2000 | Isakson et al. | |
| 6,241,969 B1 | 6/2001 | Saidi et al. | |
| 6,264,923 B1 | 7/2001 | Oliver et al. | |
| 6,264,935 B1 | 7/2001 | Chastaing et al. | |
| 6,302,331 B1 | 10/2001 | Dvorsky et al. | |
| 6,380,222 B2 | 4/2002 | Lindberg et al. | |
| 6,397,838 B1 | 6/2002 | Zimlich, Jr. et al. | |
| 6,432,963 B1 | 8/2002 | Hisamichi et al. | |
| 6,454,193 B1 | 9/2002 | Busick et al. | |
| 6,475,467 B1 | 11/2002 | Keller et al. | |
| 6,528,527 B2 | 3/2003 | Chang | |
| 6,585,958 B1 | 7/2003 | Keller et al. | |
| 6,613,795 B2 | 9/2003 | Noe et al. | |
| 6,645,466 B1 | 11/2003 | Keller et al. | |
| 6,767,901 B1 | 7/2004 | Nagano et al. | |
| 6,866,839 B2 | 3/2005 | Aberg et al. | |
| 2002/0030068 A1 | 3/2002 | Burt | |
| 2002/0053344 A1 | 5/2002 | Davies et al. | |
| 2002/0065256 A1 | 5/2002 | Karlsson et al. | |
| 2002/0077346 A1 | 6/2002 | Santus et al. | |
| 2002/0111495 A1 | 8/2002 | Magee et al. | |
| 2002/0183292 A1 | 12/2002 | Pairet et al. | |
| 2003/0008019 A1 | 1/2003 | Nishibe et al. | |
| 2003/0087848 A1 | 5/2003 | Bratzler et al. | |
| 2004/0050960 A1 | 3/2004 | Godfrey et al. | |
| 2004/0231666 A1 | 11/2004 | Barker et al. | |
| 2004/0247628 A1 | 12/2004 | Lintz et al. | |
| 2004/0266869 A1 * | 12/2004 | Montague et al. | ............ 514/554 |
| 2005/0020637 A1 | 1/2005 | Simon | |
| 2005/0175546 A1 | 8/2005 | Sambuco et al. | |
| 2006/0166953 A1 | 7/2006 | Nishibe et al. | |
| 2007/0025923 A1 | 2/2007 | Wurst et al. | |

FOREIGN PATENT DOCUMENTS

| | | |
|---|---|---|
| DE | 41 29 535 A1 | 3/1992 |
| DE | 195 41 689 A1 | 5/1996 |
| EP | 0372777 B1 | 6/1990 |
| EP | 0407028 B2 | 1/1991 |
| EP | 0 502 092 A1 | 9/1992 |
| EP | 0505321 A2 | 9/1992 |
| EP | 0553298 B1 | 8/1993 |
| EP | 0650410 B1 | 5/1995 |
| EP | 0691865 B1 | 1/1996 |
| EP | 0725725 B1 | 8/1996 |
| GB | 2247680 A * | 11/1992 |
| JP | 2001-48807 A | 2/2001 |
| WO | WO 91/04011 A1 | 4/1991 |
| WO | 91/07172 A1 | 5/1991 |
| WO | WO 91/11173 A1 | 8/1991 |
| WO | WO 91/11495 A1 | 8/1991 |

(Continued)

OTHER PUBLICATIONS

Postma et al., "Treatment of asthma by the inhaled corticosteroid ciclesonide given either in the morning or evening", 2001, Eur. Respir. J., vol. 17, pp. 1083-1088.*

(Continued)

*Primary Examiner* — Ali Soroush
(74) *Attorney, Agent, or Firm* — Nath, Goldberg & Meyer; Sheldon M. McGee; Joshua B. Goldberg

(57) ABSTRACT

The invention relates to new method of treatment of respiratory diseases, in particular the treatment of asthmatic children.

35 Claims, No Drawings

FOREIGN PATENT DOCUMENTS

| | | |
|---|---|---|
| WO | WO 91/14422 A1 | 10/1991 |
| WO | WO 92/11190 A2 | 7/1992 |
| WO | WO 93/11743 A1 | 6/1993 |
| WO | WO 94/22899 A1 | 10/1994 |
| WO | WO 95/02650 A1 | 1/1995 |
| WO | WO 96/32150 A1 | 10/1996 |
| WO | 98/09982 A1 | 3/1998 |
| WO | 98/16228 A1 | 4/1998 |
| WO | WO 98/52542 A1 | 11/1998 |
| WO | 99/25359 A1 | 5/1999 |
| WO | 99/53926 A1 | 10/1999 |
| WO | WO 00/07567 A1 | 2/2000 |
| WO | 00/17200 A1 | 3/2000 |
| WO | 00/21487 A1 | 4/2000 |
| WO | 01/22955 A2 | 4/2001 |
| WO | WO 01/28562 A1 | 4/2001 |
| WO | WO 01/28563 A1 | 4/2001 |
| WO | 01/56573 A1 | 8/2001 |
| WO | 01/78738 A1 | 10/2001 |
| WO | 01/89491 A1 | 11/2001 |
| WO | 01/98174 A1 | 12/2001 |
| WO | 01/98175 A1 | 12/2001 |
| WO | WO 02/04420 A1 | 1/2002 |
| WO | 02/28368 A1 | 4/2002 |
| WO | WO 02/30394 A2 | 4/2002 |
| WO | 02/091866 A1 | 11/2002 |
| WO | 03/006310 A1 | 1/2003 |
| WO | 03/043905 A2 | 5/2003 |
| WO | 2004/052374 A1 | 6/2004 |
| WO | WO 2004/075896 A1 | 9/2004 |

OTHER PUBLICATIONS

Dubus et al., "Loacal side-effects of inhaled corticosteroids in asthmatic children: influence of drug, age, and device", 2001, Allergy, vol. 56, pp. 944-948.*
Belvisi et al., "Soft steroids: a new approach to the treatment of inflammatory airway diseases", Sep. 2003, Pulmonary Pharmacology & Therapeutics, vol. 16, pp. 321-325.*
Agertoft et al., "Effects of long-term treatment with an inhaled corticosteroid on growth and pulmonary function in asthmatic children", May 1994, vol. 88 issue 5, abstract.*
Dietzl et al., Cliclesonide: An On-Site-Activated Steroid, 2001, New Drugs for Asthma, Allergy and COPD, vol. 31, p. 91-93.*
Agertoft, L., "Lower-Leg Growth Rate and HPA Axis Function in Children With Asthma During Treatment With Inhaled Ciclesonide," *Journal of Allergy and Clinical Immunology*, vol. 113, No. 2, p. S119 (2004).
Dent, G., "Ciclesonide," *Current Opinion in Investigational Drugs*, vol. 3, No. 1, pp. 78-83 (2002).
Mealy, N. E., "Ciclesonide," *Drugs of the Future*, vol. 26, pp. 1033-1039 (2001).
Rogers, D. F., "Pulmonary Mucus: Pediatric Perspective," *Pediatric Pulmonology*, vol. 36, p. 178-188 (2003).
Pedersen et al. "Efficacy and safety of ciclesonide once daily and fluticasone propionate twice daily in children with asthma", *Pulmonary Pharmacology & Therapeutics*, vol. 22, pp. 214-220 (2009).
Dietzel, et al., "Ciclesonide: An On-Site-Activated Steroid", Hansel TT, Barnes PJ (eds): New Drugs for Asthma, Allergy and COPD, Prog Respir Res. Basel, Karger, 2001, vol. 31, pp. 91-93.
Chapman, et al., "Effects of ciclesonide versus placebo on lung function after 12 weeks of treatment in patients with asthma", Am J Respir Crit Care Med. 2002; 165: Abstract G74, 1 page.
Chapman, et al., "Effects of ciclesonide versus placebo on lung function after 12 weeks of treatment in patients with asthma", Am J Respir Crit Care Med. 2002; 165: 1 page.
O'Connor, et al., "Management of moderate to severe bronchial asthma by ciclesonide: a 12-week trial", Am J Respir Crit Care Med. 2002; 165: Abstract G75, 1 page.
O'Connor, et al., "Management of moderate to severe bronchial asthma by ciclesonide: a 12-week trial", Am J Respir Crit Care Med. 2002; 165: 1 page.
Pauwels, et al., "Effects of inhaled ciclesonide and fluticasone propionate on cortisol secretion and $PC_{20}$ for adenosine in asthma patients", Am J Respir Crit Care Med. 2002; 165: Abstract G84, 1 page.
O'Connor, et al., "Treatment of moderate to severe asthma with ciclesonide: a long-term investigation over 52 weeks", Eur Respir J. 2002; 20(suppl 38): Abstract 2579, 1 page.
Rohatagi, et al., "Population Pharmacokinetics and Pharmacodynamics of Ciclesonide", J Clin Pharmacol, 2003; 43: pp. 365-378.
Timmer, et al., "Repeated inhalation of the new topical steroid ciclesonide does not lead to adrenal suppression in healthy subjects", Am J Respir Crit Care Med. 2000; 161: Abstract A776, 1 page.
Drollmann, et al., "Ciclesonide is effective in the treatment of bronchial asthma", Eur Respir J. 2001; 18: Abstract P681, 1 page.
Drollmann, et al., "Ciclesonide is effective in the treatment of bronchial asthma", Eur Respir J. 2001; 18: 1 page.
Wolthers, et al., "Measures of systemic activity of inhaled glucocorticosteroids in children: a comparison of urine cortisol excretion and knemometry", Respiratory Medicine, vol. 89, pp. 347-349, (1995).
Taylor, et al., "A Dose-dependent Effect of the Novel Inhaled Corticosteroid Ciclesonide on Airway Responsiveness to Adenosine-5'-Monophosphate in Asthmatic Patients", Am J Respir Crit Care Med, vol. 160, pp. 237-243, (1999).
Derom, et al., "Effects of inhaled ciclesonide and fluticasone propionate on cortisol secretion and airway responsiveness to adenosine 5' monophosphate in asthmatic patients", Pulmonary Pharmacology & Therapeutics, vol. 18, pp. 328-336, (2005).
Gelfand, et al., "Once-Daily Ciclesonide in Children: Efficacy and Safety in Asthma", J Pediatr, vol. 148, pp. 377-383, (2006).
Postma, et al., "Treatment of asthma by the inhaled corticosteroid ciclesonide given either in the morning or evening", Eur Respir J, vol. 17, pp. 1083-1088, (2001).
Weinbrenner, A., et al., "Circadian Rhythm of Serum Cortisol after Repeated Inhalation of the New Topical Steroid Ciclesonide", The Journal of Clinical Endocrinology & Metabolism, vol. 87, No. 5, pp. 2160-2163, (2002).
Agertoft, et al., "Short-term lower-leg growth rate and urine cortisol excretion in children treated with ciclesonide", J Allergy Clin Immunol, vol. 115, pp. 940-945, (2005).
von Berg, et al., "Comparison of the efficacy and safety of ciclesonide 160 µg once daily vs. budesonide 400 µg once daily in children with asthma", Pediatr Allergy Immunol, vol. 18, pp. 391-400, (2007).
Skoner, et al., "Assessment of the Long-term Safety of Inhaled Ciclesonide on Growth in Children With Asthma", Pediatrics, vol. 121, No. 1, pp. e1-e14, (2008).
Lipworth, et al., "Effect of ciclesonide and fluticasone on hypothalamic-pituitary-adrenal axis function in adults with mild-to-moderate persistent asthma", Ann Allergy Asthma Immunol., vol. 94, pp. 465-472, (2005).
Boulet, et al., "A randomized study comparing ciclesonide and fluticasone propionate in patients with moderate persistent asthma", Respiratory Medicine, vol. 101, pp. 1677-1686, (2007), Elsevier.
Pedersen, et al., "A Comparative Study of Inhaled Ciclesonide 160 µg/day and Fluticasone Propionate 176 µg/day in Children With Asthma", Pediatric Pulmonology, vol. 41, pp. 954-961, (2006), Wiley-Liss, Inc.
Lee, et al., "Airway and Systemic Effects of Hydrofluoroalkane Formulations of High-Dose Ciclesonide and Fluticasone in Moderate Persistent Asthma", Chest, vol. 127, pp. 851-860, (2005).
Szefler, et al., "Ciclesonide, a Novel Inhaled Steroid, Does Not Affect Hypothalamic-Pituitary-Adrenal Axis Function in Patients With Moderate-to-Severe Persistent Asthma", Chest, vol. 128, pp. 1104-1114, (2005).
Agertoft, et al., "Lower leg growth rates in children with asthma during treatment with ciclesonide and fluticasone propionate", Pediatr Allergy Immunol, pp. 1-7 (2009).
Autoclave standard operating procedures, 2002, pp. 1-4.
Gennaro, Remington Farmacia, Tomo 2, 19th edition, vol. 2, Ed Medica Panamericana, p. 2249.
Material Safety Data Sheet for HPMC 2019 by Shin-Etsu Co.
Difluprednate; http://en.wikipedia.org/wiki/Difluprednate; printed Nov. 23, 2009.
Vippagunta, et al., "Crystalline solids", Advanced Drug Delivery Reviews, vol. 48, pp. 3-26, (2001).

Schmidt, et al., "The New Topical Steroid Ciclesonide Is Effective in the Treatment of Allergic Rhinitis", J Clin Pharmacol, vol. 39, pp. 1062-1069, (1999).

Braga, et al., "Making crystals from crystals: a green route to crystal engineering and polymorphism", Chem. Commun., pp. 3635-3645, (2005).

Gracia-Marcos, et al., "Inhaled corticosteroids plus long-acting β2-agonists as a combined therapy in asthma", Expert Opin. Pharmacother., vol. 4, No. 1, pp. 23-39, (2003).

STN registry for Glycopyrronium, 2 pages.

STN registry for Ciclesonide, 1 page.

Gilbert, "Chapter 7: Enzyme Mechanism", Basic Concept in Biochemistry, 2nd ed., e-book, (2000).

Belvisi, et al., "Soft steroids: a new approach to the treatment of inflammatory airways diseases", Pulmonary Pharmacology & Therapeutics, vol. 16, pp. 321-325, (2003).

Armarego, et al., Purification of Laboratory Chemicals, 4th Ed., Elsevier, pp. 28-29, (1996).

Wetscher, et al., "Respiratory Symptoms in Patients with Gastroesophageal Reflux Disease following Medical Therapy and following Antireflux Surgery", The American Journal of Surgery, vol. 174, No. 6, pp. 639-643, (1997).

Simon, et al., "Soraprazan: Setting New Standards in Inhibition of Gastric Acid Secretion", The Journal of Pharmacology and Experimental Therapeutics, vol. 321, No. 3, pp. 866-874, (2007).

Maesen, et al., "Effects of formoterol in apparently poorly reversible chronic obstructive pulmonary disease", Eur Respir J, vol. 13, pp. 1103-1108, (1999).

Akpinarli, et al., "Effect of formoterol on clinical parameters and lung functions in patients with bronchial asthma: a randomised controlled trial", Arch. Dis. Child., vol. 81, pp. 45-48, (1999).

The Merck Index, 12 ed., (1996), The Merck Manual indicates that the boiling point of Acetone is 56.5° C. (p. 12, Entry 64), and the boiling point of ethanol is 78° C. (p. 641, Entry 3806).

West, et al., Solid Solutions, Solid State Chemistry and its Applications, pp. 358 and 365, (1988).

Allen, David, "Safety of Inhaled Corticosteroids in Children", Pediatric Pulmonology, 2002, 33(3), p. 208-220.

National Asthma Education and Prevention Program (NAEPP), J.Allergy Clin. Immunol., Supplement, 2002, 110(5 suppl 1), p. s147-s168.

Belvisi et al., "Soft Steroids: A New Approach to the Treatment of Inflammatory Airway Diseases", Pulmonary Pharmacology & Therapeutics, vol. 16 (6), Dec. 2003, pp. I-X. (Screenshot only—which demonstrates the online availability date of Oct. 20, 2003 provided by Elsevier Science Ltd. which was relied on by applicants in their interview dated Apr. 15, 2011 and their Response and Amendment filed Apr. 20, 2011).

Biberger, C., et al., "Efficacy and safety of ciclesonide compared with budesonide in asthma patients: a randomized 12-week study", Presented as a poster at the 99th International Conference of the American Thoracic Society (ATS); May 16-21, 2003; Seattle, Wash., Am J Respir Crit Care Med., 2003; 167: Abstract A1486.

Boulet, L-P., et al., "Ciclesonide is at least as effective as budesonide in the treatment of patients with bronchial asthma", Presented as a poster at the 99th International Conference of the American Thoracic Society (ATS); May 16-21, 2003; Seattle, Wash., Am J Respir Crit Care Med., 2003; 167: Abstract A1508.

Bundschuh, D.S., et al., "[1013] Pre-clinical anti-inflammatory activity and safety profile of the novel glucocorticoid ciclesonide", Oral Presentation: New developments in inhaled corticosteroid therapy (2:45 PM-4:45 PM) Sunday, Sep. 23, 2001, 2:45 PM, Hall 4/5.

Derom, E., et al., "Efficacy and systemic effects of ciclesonide and fluticasone in asthma patients", Oral presentation at the 11th Annual Congress of the European Respiratory Society (ERS); Sep. 22-26, 2001; Berlin, Germany, Eur Respir J., 2001; 18: Abstract 1015.

Engelstätter, R., et al., "Comparative study in asthma patients treated with inhaled ciclesonide (80 μg or 320 μg once daily) or budesonide (200 μg twice daily) for 12 weeks", Presented as a poster at the 99th International Conference of the American Thoracic Society (ATS); May 16-21, 2003; Seattle, Wash., Am J Respir Crit Care Med., 2003; 167: Abstract A1511.

Hansel, T., et al., "Once daily ciclesonide (80 μg or 320 μg) is equally effective as budesonide 200 μg given twice daily: a 12-week study in asthma patients", Eur Respir J 2003; 22 Suppl 45: 410. Plus poster presented at the 13th Annual Congress of the European Respiratory Society; Sep. 27-Oct. 1, 2003; Vienna; Abstract No. P2639.

Kanniess, F., et al., "Effect of Inhaled Ciclesonide on Airway Responsiveness to Inhaled AMP, the Composition of Induced Sputum and Exhaled Nitric Oxide in Patients with Mild Asthma", Pulmonary Pharmacology & Therapeutics, (2001), 14, 141-147, © 2001 Academic Press.

Szefler, S.J., Deputy Editor, "Early intervention for childhood asthma: Inhaled glucocorticoids as the 'preferred' medication", J Allergy Clin Immunol 1998; 102: 719-721, © 1998 by Mosby, Inc.

Ukena, D., et al., "Ciclesonide significantly improves pulmonary function when compared with budesonide: a randomized 12-week study", Eur Respir J 2003; 22 (Suppl. 45): 411s, Plus poster presented at the 13th Annual Congress of the European Respiratory Society; Sep. 27-Oct. 1, 2003; Vienna; Abstract No. P2640.

Wagener, J.S., et al., "Inhaled steroids in children: Risks versus rewards", The Journal of Pediatrics, vol. 132, No. 3, Part 1, pp. 381-383, © 1998 by Mosby, Inc.

Doull, et al., "Growth of Prepubertal Children with Mild Asthma Treated with Inhaled Beclomethasone Dipropionate", Am J Respir Crit Care Med, vol. 151, pp. 1715-1719, (1995).

Skoner, et al., "The effects of intranasal triamcinolone acetonide and intranasal fluticasone propionate on short-term bone growth and HPA axis in children with allergic rhinitis", Ann Allergy Asthma Immunol, vol. 90, pp. 56-62, (2003).

Belvisi, et al., "Pre-clinical in vivo assessment of ciclesonide, a novel corticosteroid for the treatment of asthma", European Respiratory Journal, Munksgaard International Publishers, Copenhagen, DK, vol. 18, No. Suppl. 33, Jan. 1, 2001, p. Abstr. P682, ISSN:0903-1936.

Weinbrenner, et al., "Circadian rhythm of serum cortisol after repeated inhalation of the new topical steroid ciclesonide", European Journal of Clinical Pharmacology, Springer Verlag, DE, vol. 54, Suppl., Jan. 1, 1998, p. A27, ISSN:0031-6970.

Bundschuh, D.S., et al., "Efficacy and safety profile of the novel on-site activated corticosteroid ciclesonide", American Journal of Respiratory and Critical Care Medicine, American Lung Association, New York, NY, US, vol. 163, No. 5, Suppl., Jan. 1, 2001, p. A588, ISSN:1073-449X.

European Official Action for corresponding application No. EP04766791.0, dated Sep. 26, 2011.

* cited by examiner

USE OF CICLESONIDE FOR THE TREATMENT OF RESPIRATORY DISEASES

This application was filed under 35 U.S.C. 371 as a national stage of PCT/EP2004/052172, filed Sep. 15, 2004.

FIELD OF THE INVENTION

This invention relates to a new method of treatment of respiratory diseases, in particular the treatment of asthmatic children.

BACKGROUND

U.S. Pat. No. 5,482,934 discloses pregna-1,4-diene-3,20-dione-16-17-acetal-21 esters and their use in the treatment of inflammatory conditions. The compounds have the general structure:

Formula I

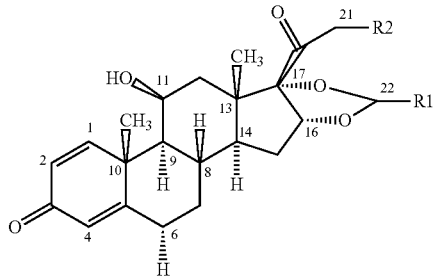

wherein R1 is 2-propyl, 1-butyl, 2-butyl, cyclohexyl or phenyl; and R2 is acetyl or isobutanoyl. Ciclesonide is the INN for a compound of formula I in which R1 is cyclohexyl and R2 is isobutanoyl with the chemical name [11β,16α(R)]-16,17-[(Cyclohexylmethylen)bis(oxy)]-11-hydroxy-21-(2-methyl-1-oxopropoxy)pregna-1,4-dien-3,20-dion.

Ciclesonide is a novel inhaled corticosteroid for asthma treatment, which is undergoing clinical evaluation. Ciclesonide has very low affinity for the glucocorticosteroid receptor but is readily converted to the active metabolite desisobutyryl-ciclesonide by esterases in the lung to provide local activity in the target organ. This activation occurs by ester cleavage at the C21 position of ciclesonide. The affinity of desisobutyrylciclesonide to the glucocorticosteroid receptor is approximately 100 times higher than that of ciclesonide. Ciclesonide is only moderately absorbed after oral administration and has low systemic activity. Concentration of the drug in the lungs is high and metabolism by liver oxidases is very high, giving the drug a low plasma half-life. Systemic activity of ciclesonide is three times lower than that of budesonide, but anti-inflammatory activity is higher for the former.

SUMMARY OF THE INVENTION

It has now been found that respiratory diseases in children may be very effectively and safely treated by administering ciclesonide to the children in need thereof in a dose of from 20 to 200 μg. In particular systemic side effects possibly associated with inhaled and intranasal corticosteroids such as growth suppression in children after long-term exposure can be reduced or completely avoided.

Subject of the invention is therefore a method for treating or preventing a respiratory disease in a patient, which patient is a child and the method comprising administering to the patient a dose of a composition containing ciclesonide, a pharmaceutically acceptable salt, solvates or physiologically functional derivative thereof, wherein the dose of the composition comprises ciclesonide in an amount of from 20 to 200 μg.

Ciclesonide (herein also referred to as active ingredient) is the INN for an active compound having the chemical name [11β,16α-(R)]-16,17-[(cyclohexylmethylene)bis(oxy)]-11-hydroxy-21-(2-methyl-1-oxopropoxy)pregna-1,4-diene-3,20-dione. Ciclesonide and its preparation are described in U.S. Pat. No. 5,482,934. According to the invention, the name ciclesonide also includes solvates of ciclesonide, physiologically functional derivatives of ciclesonide or solvates thereof. Physiologically functional derivatives of ciclesonide, which can be mentioned in connection with the present invention, are preferably chemical derivatives of ciclesonide, which have a similar physiological function as ciclesonide or an active metabolite of ciclesonide, for example the 21-hydroxy derivative of ciclesonide (hereinafter also referred to as desisobutyryl-ciclesonide=des-CIC). The 21-hydroxy compound has the chemical name 16α,17-(22R,S)-cyclohexylmethylenedioxy-11β,21-dihydroxypregna-1,4-diene-3,20-dione. This compound and its preparation are disclosed in WO 94/22899. According to the invention, the name "ciclesonide" is understood as meaning not only the pure R epimer of the compound [11β,16α]16,17-[(cyclohexylmethylene)bis(oxy)]-11-hydroxy-21-(2-methyl-1-oxopropoxy)pregna-1,4-diene-3,20-dione but also R/S epimer mixtures in any desired mixing ratio (that is the compounds [11β,16α(R)]-16,17-[(cyclohexylmethylene)bis(oxy)]-11-hydroxy-21-(2-methyl-1-oxopropoxy)pregna-1,4-diene-3,20-dione and [11β,16α(S)]-16,17-[(cyclohexylmethylene)bis(oxy)]-11-hydroxy-21-(2-methyl1-oxopropoxy)pregna-1,4-diene-3,20-dione), those being preferred which essentially consist of R epimers. According to the invention, essentially consisting of R epimers means that the proportion of S epimers in the mixture is less than or equal to 5%, preferably less than or equal to 1%.

Administering ciclesonide in a daily dose range of from 20 to 200 μg to a child afflicted with a respiratory disease results in effective treatment and or prophylaxis of the respiratory disease and avoiding systemic side effects such as growth suppression which may occur in children after long-term exposure to inhaled and intranasal corticosteroids.

Exemplary doses in connection with the invention comprise 20, 40, 60, 80, 100, 120, 140, 160, 180 or 200 μg ciclesonide. Preferably the dose comprises 40, 80 or 160 μg ciclesonide. The dose is preferably a daily dose and administered once or twice daily, preferably once daily. A once daily dose may be administered any time of the day, e.g. in the morning or preferably in the evening. The administration of a daily dose of ciclesonide in the range of from 20 to 200 μg is preferably part of a continuous treatment regimen, preferably a treatment period of more than one day, particularly preferably more than one week, e.g. a two week treatment period, a one month treatment period, a one year treatment period or a life long treatment period.

The patient in connection with the invention is a child. Child in connection with the invention refers to a human below eighteen years, e.g. seventeen years, fifteen years, ten years, nine years, five years, two years etc. Preferably child refers to a pre-pubertal human, and in particular to a human from 6 to 12 years of age.

Ciclesonide has been described for use in the treatment of respiratory diseases. Therefore, formulations of ciclesonide have use in the prophylaxis and treatment of clinical conditions for which a glucocorticosteroid is indicated. Such conditions include diseases associated with reversible airways obstruction such as asthma, nocturnal asthma, exercise-induced asthma, chronic obstructive pulmonary diseases (COPD) (e.g. chronic and wheezy bronchitis, emphysema), respiratory tract infection and upper respiratory tract disease (e.g. rhinitis, such as allergic and seasonal rhinitis). In a preferred embodiment according to the invention the respiratory disease in connection with the invention refers to asthma, preferably mild to severe asthma.

The present invention also relates to the use of ciclesonide, a pharmaceutically acceptable salt, solvates or physiologically functional derivative thereof for the manufacture of a medicament for the treatment or prevention of a respiratory disease in a patient, which patient is a child and wherein the medicament is administered at a dose of 20 to 200 µg ciclesonide.

The compositions comprising ciclesonide (also referred to as formulations, medicaments or pharmaceutical compositions) include those suitable for oral, parenteral including subcutaneous, intradermal, intramuscular, intravenous and intraaarticular, intranasal, inhalation (including fine particle dusts or mists which may be generated by means of various types of metered dose pressurised aerosols, nebulisers or insufflators), rectal and topical (including dermal, buccal, sublingual and intraocular administration) although the most suitable route may depend upon for example the condition and disorder of the recipient. The formulations may conveniently be presented in unit dosage form and may be prepared by any of the methods well known in the art of pharmacy. All methods include the step of bringing the active ingredients into association with the carrier, which constitutes one or more accessory ingredients/excipients. In general the formulations are prepared by uniformly and intimately bringing into association the active ingredient with liquid carriers or finely divided solid carriers or both and then, if necessary, shaping the product into the desired formulation.

In one embodiment ciclesonide is provided in a form suitable for inhalation. Formulations for inhalation include powder compositions, which will preferably contain lactose, and spray compositions which may be formulated, for example, as aqueous solutions or suspensions or as aerosols delivered from pressurised packs, with the use of a suitable propellant, e.g. 1, 1, 1, 2-terafluorethane, 1, 1, 1, 2, 3, 3, 3-heptafluoropropane, carbon dioxide or other suitable gas. A class of propellants, which are believed to have minimal ozone-depleting effects in comparison to conventional chlorofluorocarbons comprise hydrofluorocarbons and a number of medicinal aerosol formulations using such propellant systems are disclosed in, for example, EP 0372777, WO91/04011, WO91/11173, WO91/11495, WO91/14422, WO93/11743, and EP-0553298. These applications are all concerned with the preparation of pressurised aerosols for the administration of medicaments and seek to overcome problems associated with the use of this new class of propellants, in particular the problems of stability associated with the pharmaceutical formulations prepared. The applications propose, for example, the addition of one or more of excipients such as polar cosolvents or wetting agents (e.g. alcohols such as ethanol), alkanes, dimethyl ether, surfactants (including fluorinated and non-fluorinated surfactants, carboxylic acids such as oleic acid, polyethoxylates etc.) or bulking agents such as a sugar (see for example WO02/30394) and vehicles such as cromoglicic acid and/or nedocromil which are contained at concentrations, which are not therapeutically and prophylactically active (see WO00/07567). For suspension aerosols, the active ingredients should be micronised so as to permit inhalation of substantially all of the active ingredients into the lungs upon administration of the aerosol formulation, thus the active ingredients will have a mean particle size of less than 100 microns, desirably less than 20 microns, and preferably in the range 0.7 to 10 microns, for example, 1 to 5 microns.

WO 98/52542 is related to pharmaceutical compositions comprising a therapeutically effective amount of ciclesonide or a related compound and a hydrofluorocarbon propellant, preferably selected from 1,1,1,2-tetrafluoroethane, 1,1,1,2,3,3,3-heptafluoropropane and a mixture thereof, and cosolvent, preferably ethanol, in an amount effective to solubilize ciclesonide and optionally a surfactant. In a preferred embodiment ciclesonide is administered in a composition according to WO98/52542.

Ciclesonide is generally present in the formulation at a concentration, which allows administration of a dose of from 20 to 200 µg. Such formulation generally comprises ethanol in an amount effective to solubilize the ciclesonide. The propellant preferably includes a hydrofluoroalkane, in particular Propellant 134a, Propellant 227 or a mixture thereof. In the case of a mixture the ratio of Propellant 134a to Propellant 227 is generally in a range from 75:25 w/w to 25:75 w/w. The formulations may contain surfactant such as oleic acid, but may be also free of surfactant. The formulations are preferably free of other excipients.

The formulations may be manufactured by preparing a drug concentrate of the active ingredients with ethanol and adding this concentrate to the pre-chilled propellant in a batching vessel. Preferably a solution of the ciclesonide in the cosolvent is added to the prechilled propellant in a batching vessel. The resulting formulation is filled into vials. Alternatively the formulations may be prepared by adding the required quantity of active ingredient into an aerosol vial, crimping a valve on the vial and introducing a premixed blend of propellant and ethanol through the valve. The vial is placed in an ultrasonic bath to ensure solubilisation of ciclesonide.

In another embodiment preferred compositions for aerosol delivery contain the active ingredient in particulate form, and 1,1,1,2-tetrafluoroethane, 1,1,1,2,3,3,3-heptalluoropropane or mixtures thereof as propellant. Such formulation generally comprises from 0.01 to 5% (w/w relative to the total weight of the formulation) of polar cosolvent, in particular ethanol. In a preferred embodiment no or less than 3% w/w of polar cosolvent, in particular ethanol is contained. Especially preferred compositions for aerosol delivery consist of particulate active ingredient, and 1, 1, 1, 2-tetrafluoroethane, 1, 1, 1, 2, 3, 3, 3-heptafluorpropane or mixtures thereof as propellant and optionally a surfactant (preferably oleic acid). In the case of a mixture the ratio of Propellant 134a to Propellant 227 is generally in a range from 7525 w/w to 25:75 w/w.

The formulations may be prepared by adding the required quantity of active ingredient into an aerosol vial, crimping a valve on the vial and introducing propellant or optionally a pre-mixed blend of propellant and optionally the cosolvent and surfactant through the valve.

Canisters generally comprise a container capable of withstanding the vapour pressure of the propellant, such as plastic or plastic-coated glass bottle or a metal can, for example an aluminium can which may optionally be anodised, lacquer-coated and/or plastic-coated, which container is closed with a metering valve. Canisters may be coated with a fluorocarbon polymer as described in WO 96/32150, for example, a co-polymer of polyethersulphone (PES) and polytetrafluoroethylene (PTFE). Another polymer for coating that may be contemplated is FEP (fluorinated ethylene propylene).

The metering valves are designed to deliver a metered amount of the formulation per actuation and incorporate a gasket to prevent leakage of propellant through the valve. The gasket may comprise any suitable elastomeric material such as for example low density polyethylene, chlorobutyl, black and white butadiene-acrylonitrile rubbers, butyl rubber and neoprene. Thermoplastic elastomer valves as described in WO92/11190 and valves containing EPDM rubber as described in WO95/02650 may be suitable. Suitable valves are commercially available from manufacturers well known in the aerosol industry, for example, from Valois, France (eg. DF10, DF30, DF60), Bespak pic, UK (eg. BK300, BK356, BK357) and 3M-Neotechnic Ltd, UK (eg. Spraymiser).

Valve seals, especially the gasket seal and also the seals around the metering chamber, can be manufactured of a material, which is inert to and resists extraction into the contents of the formulation, especially when the contents include ethanol.

Valve materials, especially the material of manufacture of the metering chamber, can be manufactured of a material, which is inert to and resists distortion by contents of the formulation, especially when the contents include ethanol. Particularly suitable materials for use in manufacture of the metering chamber include polyesters eg polybutyleneterephthalate (PBT) and acetals, especially PBT.

Materials of manufacture of the metering chamber and/or the valve stem may desirably be fluorinated, partially fluorinated or impregnated with fluorine containing substances in order to resist drug deposition.

Valves, which are entirely or substantially composed of metal components (eg Spraymiser, 3M-Neotechnic), are especially preferred for use according to the invention.

Intranasal sprays or nasal drops may be formulated with aqueous or non-aqueous vehicles with or without the addition of agents such as thickening agents, buffer salts or acid or alkali to adjust the pH, isotonicity adjusting agents, preservatives or anti-oxidants. Suitable aqueous formulations for ciclesonide for application to mucosa are for example disclosed in WO01/28562 and WO01/28563.

In another embodiment of the invention the pharmaceutical formulation comprising the ciclesonide in as a dry powder, i.e. ciclesonide is present in a dry powder comprising finely divided ciclesonide optionally together with a finely divided pharmaceutically acceptable carrier, which is preferably present and may be one or more materials known as carriers in dry powder inhalation compositions, for example saccharides, including monosaccharides, disaccharides, polysaccharides and sugar alcohols such as arabinose, glucose, fructose, ribose, mannose, sucrose, trehalose, lactose, maltose, starches, dextran or mannitol. An especially preferred carrier is lactose, particularly in the form of the monohydrate. The dry powder may be in capsules of gelatine or plastic, or in blisters, for use in a dry powder inhalation device, preferably in dosage units of the ciclesonide together with the carrier in amounts to bring the total weight of powder in each capsule to from 5 mg to 50 mg. Alternatively the dry powder may be contained in a reservoir of a multi-dose dry powder inhalation device. Capsules and cartridges of for example gelatin, or blisters of for example laminated aluminium foil, for use in an inhaler or insulator may be formulated containing a powder mix of the active ingredients and a suitable powder base such as lactose or starch, preferably lactose. In this aspect, the active ingredient is suitably micronised so as to permit inhalation of substantially all of the active ingredients into the lungs upon administration of the dry powder formulation, thus the active ingredient will have a particle size of less than 100 μm, desirably less than 20 μm, and preferably in the range 1 to 10 μm. The solid carrier, where present, generally has a maximum particle diameter of 300 μm, preferably 200 μm, and conveniently has a mean particle diameter of 40 to 100 μm, preferably 50 to 75 μm. The particle size of the active ingredient and that of a solid carrier where present in dry powder compositions, can be reduced to the desired level by conventional methods, for example by grinding in an air-jet mill, ball mill or vibrator mill, microprecipitation, spray drying, lyophilisation or recrystallisation from supercritical media.

Where the inhalable form of the composition of the invention is the finely divided particulate form, the inhalation device may be, for example a dry powder inhalation device adapted to deliver dry powder from a capsule or blister containing a dosage unit of the dry powder or a multi-dose dry powder inhalation device. Such dry powder inhalation devices are known in the art. Examples which may be mentioned are Cyclohaler®, Diskhaler® Rotadisk®, Turbohaler® or the dry powder inhalation devices disclosed EP 0 505 321, EP 407028, EP 650410, EP 691865 or EP 725725 (Ultrahaler®).

Formulations for inhalation by nebulization may be formulated with an aqueous vehicle with the addition of agents such as acid or alkali, buffer salts, isotonicity adjusting agents or antimicrobials. They may be sterilised by filtration or heating in an autoclave. Suitable technologies for this type of administration are known in the art. As an example the Mystic® technology is to be mentioned (see for example U.S. Pat. No. 6,397,838, U.S. Pat. No. 6,454,193 and U.S. Pat. No. 6,302,331).

Preferred unit dosage formulations are those containing a pharmaceutical effective dose, as hereinbefore recited, or an appropriate fraction thereof, of the active ingredient. Thus, in the case of formulations designed for delivery by metered dose pressurised aerosols, one actuation of the aerosol may deliver half of the therapeutical effective amount such that two actuations are necessary to deliver the therapeutically effective dose.

It should be understood that in addition to the ingredients particularly mentioned above, the formulations of this invention may include other agents conventional in the art having regard to the type of formulation in question. Furthermore, the claimed formulations include bioequivalents as defined by the US Food and Drugs Agency.

The invention will now be illustrated by the following examples without restricting it.

EXAMPLES

Example 1

Ciclesonide Metered Dose Inhaler (HFA-MDI)

Ciclesonide is provided as pharmaceutical product comprising an aerosol vial equipped with a dispensing valve and containing the following formulation:

| | |
|---|---|
| Ciclesonide | 1.000 mg/ml |
| Ethanol | 94.800 mg/ml |
| P134a | 1090.200 mg/ml |

Example 2

Clinical Study in Children with Asthma

The present study was conducted to determine the effects of ciclesonide at doses intended for the use in children on lower leg growth rate and HPA function in children with mild asthma.

METHODS: In a double blind, randomized, placebo-controlled, 4-period cross-over study, 24 children, 6 to 12 years of age, received ciclesonide 40, 80 and 160 μg or placebo via HFA-MDI once daily in the evening. Each 2-week treatment period was followed by a 2-week washout. Knemometry was performed at the beginning and the end of each treatment period. Cortisol levels in 12 h overnight urine were measured at the end of each treatment period.

RESULTS: No statistically significant differences were seen in lower-leg growth rates between any of the ciclesonide treatments and placebo; lower leg growth rates were 0.412 mm/week (placebo), 0.425 mm/week (ciclesonide 40 μg), 0.397 mm/week (80 μg), 0.370 mm/week (160 μg). There was no statistically significant dose-response effect. Likewise, no difference between the various treatments and no dose-dependency was found for urinary free cortisol adjusted for creatinine. All treatments were well tolerated.

CONCLUSIONS: Short-term lower leg growth rate and HPA-axis function of pre-pubertal children with mild asthma are not affected by treatment with ciclesonide in a dose range intended for the use in children.

Although the invention has been described in terms of preferred formulations and ingredients, it will be understood that these are not intended to be limiting. To the contrary, those skilled in the art will understand that various optional ingredients may be included, such as flavouring agents, preservatives, additional active ingredients, and the like, while still embodying the present invention.

The invention claimed is:

1. A method for treating a respiratory disease in a child while reducing or avoiding systemic side effects on said child's growth rate, comprising administering to the child a dose of a composition containing ciclesonide as the sole active ingredient, or a pharmaceutically acceptable salt thereof, wherein the dose of the composition comprises ciclesonide in an amount of from 20 to 200 μg, and wherein ciclesonide consists essentially of its R-epimer.

2. The method according to claim 1, wherein the dose comprises 20, 40, 60, 80, 100, 120, 140, 160, 180 or 200 μg of ciclesonide.

3. The method according to claim 1, wherein the dose comprises 40, 80 or 160 μg of ciclesonide.

4. The method according to claim 1, wherein the child is a pre-pubertal human.

5. The method according to claim 1, wherein the child is a human from 6 to 12 years of age.

6. The method according to claim 1, wherein the dose is a daily dose in a continuous treatment regimen.

7. The method according to claim 6, wherein the treatment period is more than one day.

8. The method according to claim 7, wherein the treatment period is more than one week.

9. The method according to claim 1, wherein the composition comprises a pharmaceutically acceptable carrier and/or one or more excipients.

10. The method according to claim 1, wherein the dose is administered once daily.

11. The method according to claim 1, wherein the composition is suitable for administration by inhalation.

12. The method according to claim 11 wherein the composition is a pharmaceutical aerosol formulation comprising a therapeutically effective amount of ciclesonide and a hydrofluorocarbon propellant and cosolvent in an amount effective to solubilize ciclesonide and optionally a surfactant.

13. The method according to claim 12, wherein the cosolvent is ethanol.

14. The method according to claim 11 wherein the composition is a pharmaceutical aerosol formulation comprising particles of ciclesonide in a therapeutically effective amount and a hydrofluorocarbon propellant and 0.01 to 5% w/w based upon propellant of polar cosolvent and optionally a surfactant.

15. The method according to claim 11 wherein the composition is a dry powder and the carrier is a saccharide.

16. The method according to claim 11 wherein the carrier is lactose monohydrate.

17. The method according to claim 1, wherein the respiratory disease is selected from the group consisting of asthma, nocturnal asthma, exercise-induced asthma, chronic obstructive pulmonary diseases (COPD), chronic bronchitis, wheezy bronchitis, emphysema, respiratory tract infection, upper respiratory tract disease, rhinitis, and allergic and seasonal rhinitis.

18. The method according to claim 1, wherein the respiratory disease is mild or moderate asthma.

19. The method according to claim 12 wherein the hydrofluorocarbon propellant is selected from the group consisting of 1,1,1,2-tetrafluoroethane, 1,1,1,2,3,3,3-heptafluoropropane and mixtures thereof.

20. The method according to claim 14 wherein the hydrofluorocarbon propellant is selected from the group consisting of 1,1,1,2-tetrafluoroethane, 1,1,1,2,3,3,3-heptafluoropropane and mixtures thereof.

21. The method according to claim 1, wherein the composition is an intranasal spray or nasal drops.

22. The method according to claim 21, wherein the composition is an aqueous formulation for application to mucosa.

23. The method according to claim 21, wherein the composition is a non-aqueous formulation for application to mucosa.

24. The method according to claim 1, wherein the child is a human below the age of eighteen years.

25. The method according to claim 1, wherein the respiratory disease is rhinitis.

26. The method according to claim 1, wherein the respiratory disease is allergic rhinitis.

27. The method according to claim 1, wherein the respiratory disease is seasonal allergic rhinitis.

28. The method according to claim 1, wherein the amount of ciclesonide administered is a daily dose.

29. The method according to claim 2, wherein the amount of ciclesonide administered is a daily dose.

30. The method according to claim 3, wherein the amount of ciclesonide administered is a daily dose.

31. The method according to claim 1, wherein the dose is administered twice daily.

32. The method according to claim 11, 12, 13 or 14, wherein the composition is suitable for oral administration.

33. The method according to claim 11, 12, 13 or 14, wherein the composition is suitable for intranasal administration.

34. The method according to claim 26, wherein the composition is an aqueous intranasal spray, wherein the dose of the composition is administered once daily and comprises ciclesonide in an amount of 200 μg.

35. The method according to claim 13, wherein the respiratory disease is asthma, and wherein the dose of the composition is administered orally twice daily and comprises ciclesonide in an amount of 80 μg or 160 μg.

* * * * *

UNITED STATES PATENT AND TRADEMARK OFFICE
CERTIFICATE OF CORRECTION

| | | |
|---|---|---|
| PATENT NO. | : 8,371,292 B2 | Page 1 of 1 |
| APPLICATION NO. | : 10/571311 | |
| DATED | : February 12, 2013 | |
| INVENTOR(S) | : Wilhelm Wurst et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1234 days.

Signed and Sealed this
Twenty-eighth Day of October, 2014

Michelle K. Lee
*Deputy Director of the United States Patent and Trademark Office*